(12) United States Patent
Luther et al.

(10) Patent No.: US 8,989,860 B2
(45) Date of Patent: Mar. 24, 2015

(54) MULTISITE HEART PACING WITH ADJUSTABLE NUMBER OF PACING SITES FOR TERMINATING HIGH FREQUENCY CARDIAC ARRHYTHMIAS

(75) Inventors: Stefan Luther, Göttingen (DE); Valentin Krinski, Villeneuve Loubet (FR); Eberhard Bodenschatz, Göttingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 307 days.

(21) Appl. No.: 13/399,229

(22) Filed: Feb. 17, 2012

(65) Prior Publication Data

US 2012/0197328 A1 Aug. 2, 2012

Related U.S. Application Data

(63) Continuation-in-part of application No. 12/040,007, filed on Feb. 29, 2008, now abandoned.

(60) Provisional application No. 60/892,855, filed on Mar. 3, 2007.

(51) Int. Cl.
*A61B 5/04* (2006.01)
*A61N 1/362* (2006.01)
*A61B 5/046* (2006.01)
(Continued)

(52) U.S. Cl.
CPC .............. *A61N 1/3622* (2013.01); *A61B 5/046* (2013.01); *A61N 1/3962* (2013.01); *A61B 5/0488* (2013.01)
USPC .................................................. 607/4; 607/5

(58) Field of Classification Search
USPC .................................................. 607/4–5, 15
See application file for complete search history.

(56) References Cited

U.S. PATENT DOCUMENTS

| 4,996,984 A | 3/1991 | Sweeney |
| 5,275,621 A | 1/1994 | Mehra |

(Continued)

FOREIGN PATENT DOCUMENTS

| EP | 0 393 265 A1 | 10/1990 |
| EP | 1 062 971 B1 | 12/2000 |

(Continued)

OTHER PUBLICATIONS

Sepulveda, NG; Roth, BJ; Wiskwo, JP: Current injection into a two-dimensional anisotropic bidomain. Biophys J. 55 (5), 987-99. 1989.

(Continued)

*Primary Examiner* — Rex R Holmes

(57) ABSTRACT

High frequency cardiac arrhythmias and fibrillations are terminated by electric field pacing pulses having an order of magnitude less energy than a conventional cardioversion or defibrillation energy. The frequency and number of the pulses are selected based on a frequency analysis of a present high frequency cardiac arrhythmia or fibrillation. The energy of the pulses is selected from $\frac{1}{400}$ to $\frac{1}{2}$ of the conventional defibrillation energy, and the amplitude of the electric field pacing pulses are selected such as to activate a multitude of effective pacing sites in the heart tissue per each pacing electrode. The number and locations of the effective pacing sites in the heart tissue are regulated by the amplitude of the electric field pacing pulses, and by an orientation of the electric field of the pulses.

6 Claims, 9 Drawing Sheets

Obstacle size

(51) Int. Cl.
*A61N 1/39* (2006.01)
*A61B 5/0488* (2006.01)

(56) References Cited

U.S. PATENT DOCUMENTS

| | | | |
|---|---|---|---|
| 5,489,293 A | 2/1996 | Pless et al. | |
| 5,562,708 A * | 10/1996 | Combs et al. | 607/4 |
| 5,855,592 A * | 1/1999 | McGee et al. | 607/4 |
| 6,512,957 B1 | 1/2003 | Witte | |
| 6,587,720 B2 * | 7/2003 | Hsu et al. | 607/4 |
| 6,873,873 B2 * | 3/2005 | Hsu et al. | 607/4 |
| 7,006,867 B1 | 2/2006 | Kroll | |
| 7,020,517 B2 | 3/2006 | Weiner | |
| 7,120,490 B2 | 10/2006 | Chen et al. | |
| 7,127,292 B2 | 10/2006 | Warman et al. | |
| 7,142,911 B2 * | 11/2006 | Boileau et al. | 607/3 |
| 7,142,928 B2 | 11/2006 | Sharma et al. | |
| 7,386,343 B1 * | 6/2008 | Kroll et al. | 607/4 |
| 7,418,293 B2 | 8/2008 | Sweeney | |
| 2003/0163165 A1 | 8/2003 | Bornzin et al. | |
| 2006/0100670 A1 | 5/2006 | Sweeney | |
| 2010/0042172 A1 | 2/2010 | Armoundas | |
| 2011/0009916 A1 | 1/2011 | Efimov et al. | |

FOREIGN PATENT DOCUMENTS

| | | |
|---|---|---|
| EP | 2 177 243 A2 | 4/2010 |
| GB | 2 025 236 A | 1/1980 |
| WO | 2008/035070 A1 | 3/2008 |

OTHER PUBLICATIONS

Allessie M. et al.: Regional control of atrial fibrillation by rapid pacing in conscious dogs. Circulation. 1991; 84: 1689-1697.
Daoud EG et al.: Response of Type I atrial fibrillation to atrial pacing in humans. Circulation, 1996; 94: 1036-1040.
Disertori M. et al.: Antitachycardia pacing therapies to terminate atrial tachyarrhythmias: the AT500 Italian Heart Registry. European Heart Journal Supplements. 2001; 3: 16-24.
Pumir, A; Krinsky, V.: Unpinning of a rotating wave in cardiac muscle by an electric field. J. Theor. Biol., 199, 311-319, 1999 S.
Takagi et al.: Unpinning and removal of a rotating wave in cardiac muscle. Phys. Rev. Let. 2004, 93 (5), 058101.

* cited by examiner

MULTISITE HEART PACING WITH ADJUSTABLE NUMBER OF PACING SITES FOR TERMINATING HIGH FREQUENCY CARDIAC ARRHYTHMIAS

CROSS REFERENCE TO RELATED APPLICATIONS

This application is a continuation-in-part (CIP) to U.S. patent application Ser. No. 12/040,007 filed on Feb. 29, 2008 and claiming priority to Provisional Application No. 60/892,855, filed on Mar. 3, 2007.

FIELD OF THE INVENTION

The present invention generally relates to a method of and an apparatus for cardiac multi site pacing with an adjustable number of pacing sites. More particular, the present invention generally relates to a method of and an apparatus for terminating paroxysmal atrial fibrillation (AF) and ventricular fibrillation (VF).

BACKGROUND OF THE INVENTION

The only successful known method of terminating high frequency cardiac arrhythmias is cardioversion also known as defibrillation. In defibrillation the heart is reset by a single high voltage and high current electric shock of a high energy which is also designated as the conventional cardioversion or defibrillation energy here. In extra-corporal defibrillation, the voltage of such an electric shock typically amounts to about 1000 Volts, its current to about 30 Amperes, and the conventional or state of art defibrillating energy to about 360 Joules. For intracardiac defibrillation, the conventional or state of art defibrillating energy is about 5 to 20 Joules. In both cases, the electric field during the electric shock is about 6 V/cm. A discharge of a defibrillator in a conscious patient is painful and extremely unpleasant. It also has potential tissue damaging effects.

Antitachycardia pacing (ATP) is a much more gentle known method. It is not painful, because the energy of its pacing pulses is several orders of magnitude less than the conventional cardioversion or defibrillation energy. ATP, however, is only successful against low frequency arrhythmias (frequency not higher than 4 Hz). Its success rate decreases fast with increasing frequency of the arrhythmia, and high frequency cardiac arrhythmias (frequencies larger 4 Hz), and atrial fibrillation (AF) and ventricular fibrillation (VF) cannot be terminated by ATP.

Allessie M, et al., Regional control of atrial fibrillation by rapid pacing in conscious dogs. Circulation. 1991; 84:1689-1697 have tried to entrain AF, i.e. to control it by pacing pulses at a high frequency. They were successful only locally, i.e. in a small vicinity (several cm) of the pacing electrode; outside of this vicinity AF is not entrained.

An obvious solution to this problem would be to pace AF from so many sites, i.e. with so many pacing electrodes, that they cover the atrium dense enough. But many implanted pacing electrodes and their connecting wires would severely damage a contracting heart.

U.S. Pat. No. 4,996,984 issued to Sweeney discloses a method of defibrillating a mammal in need of defibrillation. This known method comprises first determining the mammal's fibrillation cycle length; and then administering to said mammal two bursts of electrical current delivered sequentially to said mammal. The current of each of the burst is from about 4 Amperes to about 10 Amperes; the voltage of each burst is from about 200 Volts to about 300 Volts; the duration of each burst is from about 8 milliseconds to about 15 milliseconds; and the timing between the two bursts is adjusted to about 75% of the mammal's fibrillation cycle length. The energy of each of the bursts which are administered within the body of the mammal is reported to be as low as 3 Joules. The fibrillation cycle length of a fibrillating heart is obtained using fast Fourier transformation, for example.

U.S. Pat. No. 7,418,293 issued to Sweeney discloses further reducing the electric energy required for terminating a fibrillation event as compared to a single pulse used for defibrillation by means of multiple pulse defibrillation. The reported minimum energy per pulse in multiple pulse defibrillation is about a quarter of the energy required for defibrillation by means of a single pulse.

U.S. Pat. No. 7,006,867 issued to Kroll discloses a method for overdrive pacing a patient's heart using an implantable cardiac stimulation device connected to the heart. The known method comprises disposing a plurality of leads within an atrium of the heart, sensing atrial activity through at least one of the plurality of leads, determining an overdrive pacing rate based in part on the sensed atrial activity, and delivering atrial pacing pulses to the atrium through at least one of the plurality of leads at the overdrive pacing rate. A first one of the plurality of leads may be coupled to the interatrial septum of the atrium, a second one of the plurality of leads may be coupled to the sinus node of the atrium, and a third one of the plurality of leads may be coupled to the left atrium through the coronary sinus/great vein of the patient's heart. The known method includes multiple site sensing and/or multiple site pacing. In one embodiment, the delivering step comprises delivering the atrial pacing pulses in a staggered manner, with a first pulse delivered to a first one of the plurality of leads and a second pulse delivered to a second one of the plurality of leads, and with a predetermined time delay defined between delivery of the first and second pulses.

A method of terminating high frequency arrhythmias and AF is needed that operates at an energy level much lower than that of conventional cardioversion/defibrillation and that is nevertheless able to terminate arrhythmias that ATP cannot terminate. It would be highly appreciated if the energy level could remain below the pain threshold.

SUMMARY OF THE INVENTION

The present invention relates to a method of cardiac multi site pacing with an adjustable number of pacing sites, the method comprising delivering a multitude of electric field pacing pulses to the heart whose amplitude is selected from about 0.15 to about 1.25 V/cm such as to activate a multitude of heterogeneities naturally existing in the heart as effective pacing sites in the heart tissue by each of the electric field pacing pulses.

The present invention satisfies a need for a technique that permits to terminate high frequency arrhythmias and, in particular, AF with a pulse energy much smaller than that of conventional cardioversion/defibrillation. The method of the present invention may, however, also be used in other heart pacing applications.

In a more particular aspect, the present invention relates to a method of terminating high frequency cardiac arrhythmias and fibrillation by multisite electric field pacing. This method comprises determining a real time Fourier spectrum of fibrillation; selecting several highest frequencies $f\_i$ in the spectrum; selecting the pacing pulse energy in the range $1/400$-$1/2$ of the state of art defibrillation energy; selecting pacing parameters, including a number of pulses N and a pacing frequency F, based on the several determined highest frequencies f_i in the Fourier spectrum; and delivering the pulses to the fibrillating heart to terminate the arrhythmia.

The method of the present invention is designated as anti fibrillation pacing (AFP). In another more particular aspect, the present invention relates to an anti fibrillation pacing (AFP) method of terminating high frequency cardiac arrhythmias and fibrillations. This method comprises determining a frequency spectrum of a high frequency cardiac arrhythmia or fibrillation of the heart; selecting a frequency of electric field pacing pulses based on the frequency spectrum; selecting an energy of the electric field pacing pulses from about 0.01 to about 1 Joules; selecting an amplitude of the electric field pacing pulses from about 0.15 to about 0.5 V/cm such as to activate a multitude of heterogeneities naturally existing in the heart as effective pacing sites in the heart tissue by each of the electric field pacing pulses; and delivering 4 to 8 of the electric field pacing pulses having the selected frequency, energy and amplitude to the heart. Here too, selecting a frequency of electric field pacing pulses based on the frequency spectrum may particularly include selecting a frequency of the electric field pacing pulses based on several (e.g., three) selected highest frequencies in a Fourier spectrum of the high frequency cardiac arrhythmia or fibrillation.

The present invention also relates to an apparatus for cardiac multi site pacing with adjustable number of pacing sites. This apparatus comprises a pulse generator generating electric field pacing pulses whose amplitude is selected from about 0.15 to about 1.25 V/cm such as to activate a multitude of heterogeneities naturally existing in a biological tissue as effective pacing sites by each of the electric field pacing pulses; and a pacing electrode connected to the pulse generator and configured to deliver a multitude of the electric field pacing pulses to a heart.

The apparatus of the present invention may be realised as an implanted device or as an external device. Particularly it may be used for AFP.

The invention suggests to use heterogeneities naturally existing in the heart as pacing sites. Pacing from heterogeneities naturally existing in the heart has some advantages over conventional pacing:

- a multisite pacing can be achieved without connecting many electrodes to the heart;
- the number and position of pacing sites can be regulated by changing the amplitude and the direction of the electric field of the electric field pulses;
- an energy of the electric field pulses needed for terminating high frequency arrhythmias and AF is up to 400 times smaller than that used in cardioversion/defibrillation.

In heart preparations, AFP terminates high frequency cardiac arrhythmias and AF with pulses of much smaller energy than the cardioversion/defibrillating pulse, and at a much higher success rate than conventional ATP.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

Between d) and e) the direction of the electric field (long arrow) is changed. Amplitude of the electric field is the same E=0.5 V/cm. The depicted results were obtained from numerical simulations of the LR model.

Figure 3:
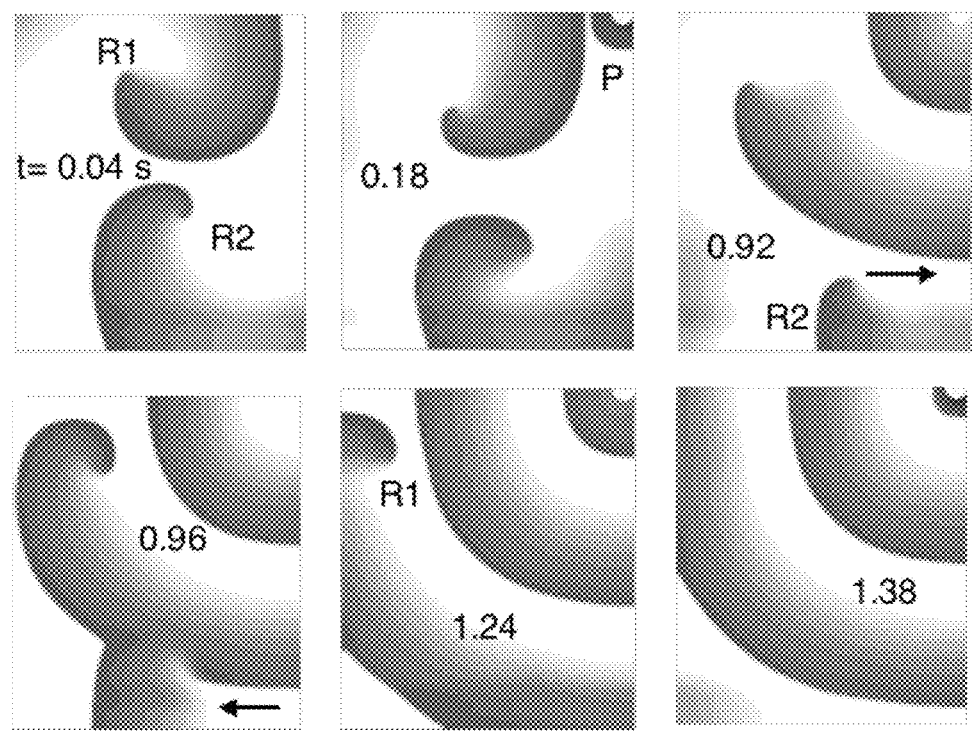

FIG. 3 illustrates how pacing from heterogeneities (virtual electrodes) removes rotating waves. t=0.04 s: R1 and R2 designate rotating waves. t=0.18 s: P designates a pacing wave emitted from a heterogeneity (depicted as a white circle partially visible in the top right corner of the drawing) by an electric field pulse E=1.25 V/cm. t=0.92 s: The tip of R2 approaches the front of the pacing wave and collides with it. t=0.96 s: The tip of R2 has disappeared but a new wave break is formed at the front of R1. Thus, a jump of the wave break position and of its orientation (arrows) has been induced (compare arrows at t=0.92 s and t=0.96 s). t=1.24 s: The rotating wave R2 is terminated. R1 is in now in a position to be terminated by the same mechanism. t=1.38 s: Rotating waves are removed. Pacing waves emitted from the heterogeneity (a white circle at the upper right corner) entrain the whole medium. The depicted results were obtained from numerical simulations of the LR model.

Figure 4:
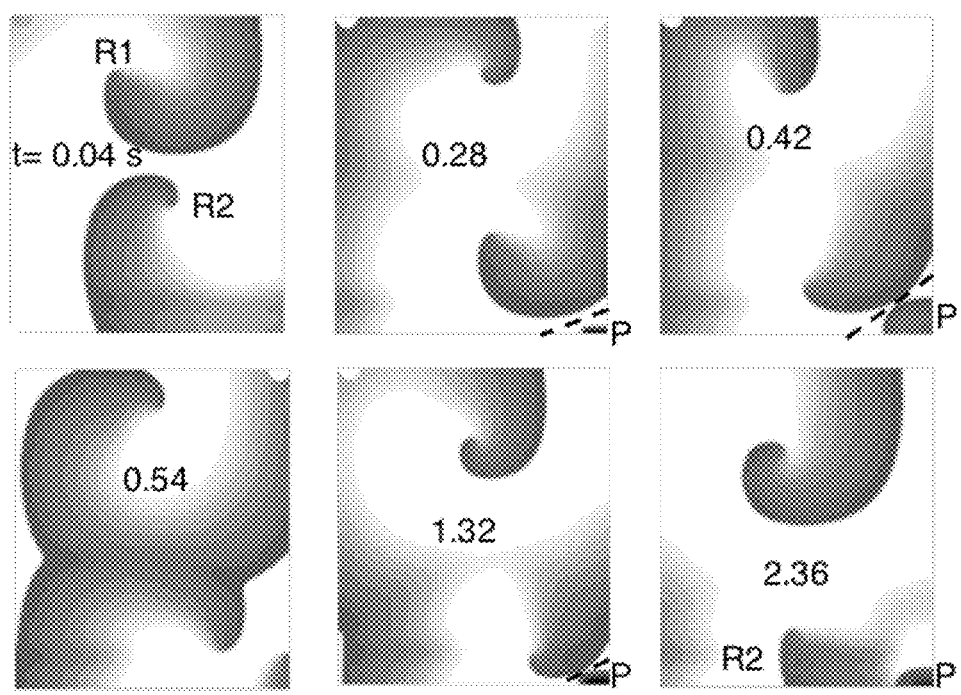

FIG. 4 illustrates that pacing from an ATP fixed lead does not remove rotating waves. t=0.04 s: same as in FIG. 3. t=0.28 s: P designates a first pacing wave emitted from a fixed electrode (right lower corner). A dashed line indicates a boundary of the region paced by this wave. t=0.42 s: By a second pacing wave, the size of the paced region is increased. t=0.54 s: A third pacing wave decays. A fuzzy front is seen instead of a sharp front observed with propagating waves. t=1.32 s: The size of the paced region has decreased (as compared to t=0.42 s). t=2.36 s: The rotating waves are not removed. A small paced region (at the lower right corner) enlarges and shrinks quasi periodically. The depicted results were obtained from numerical simulations of the LR model. All simulation parameters were the same as in FIG. 3.

Figure 5:
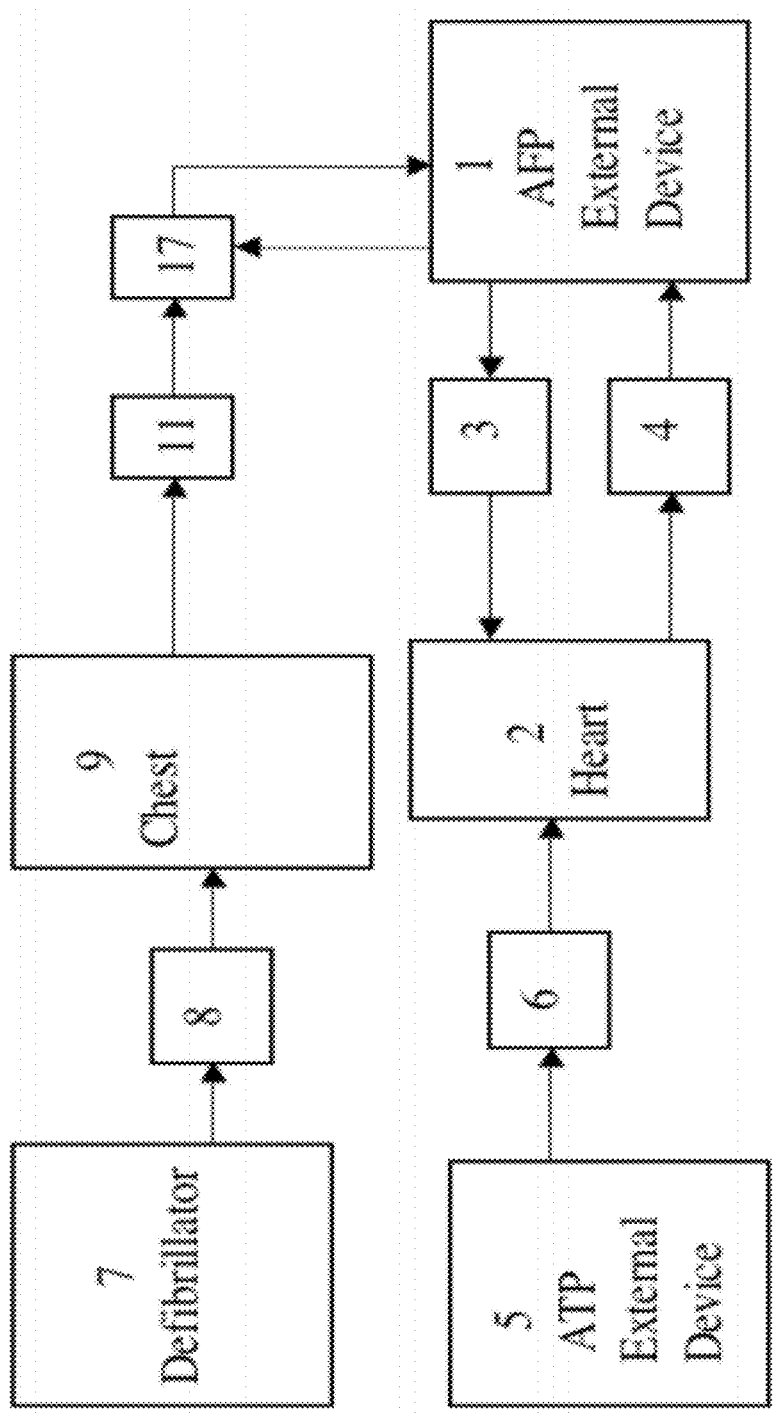

FIG. 5 is a diagram illustrating an embodiment of controlling high frequency cardiac arrhythmias by an AFP external device. A standard ATP external device 5 and the AFP external device 1 according to the present invention are connected to a heart. The further items schematically depicted in FIG. 5 are a defibrillating electrode 3, a diagnostic catheter 4, a catheter with stimulating electrodes 6, a paddle electrode, an ECG electrode 11, and a switch 17.

Figure 6:
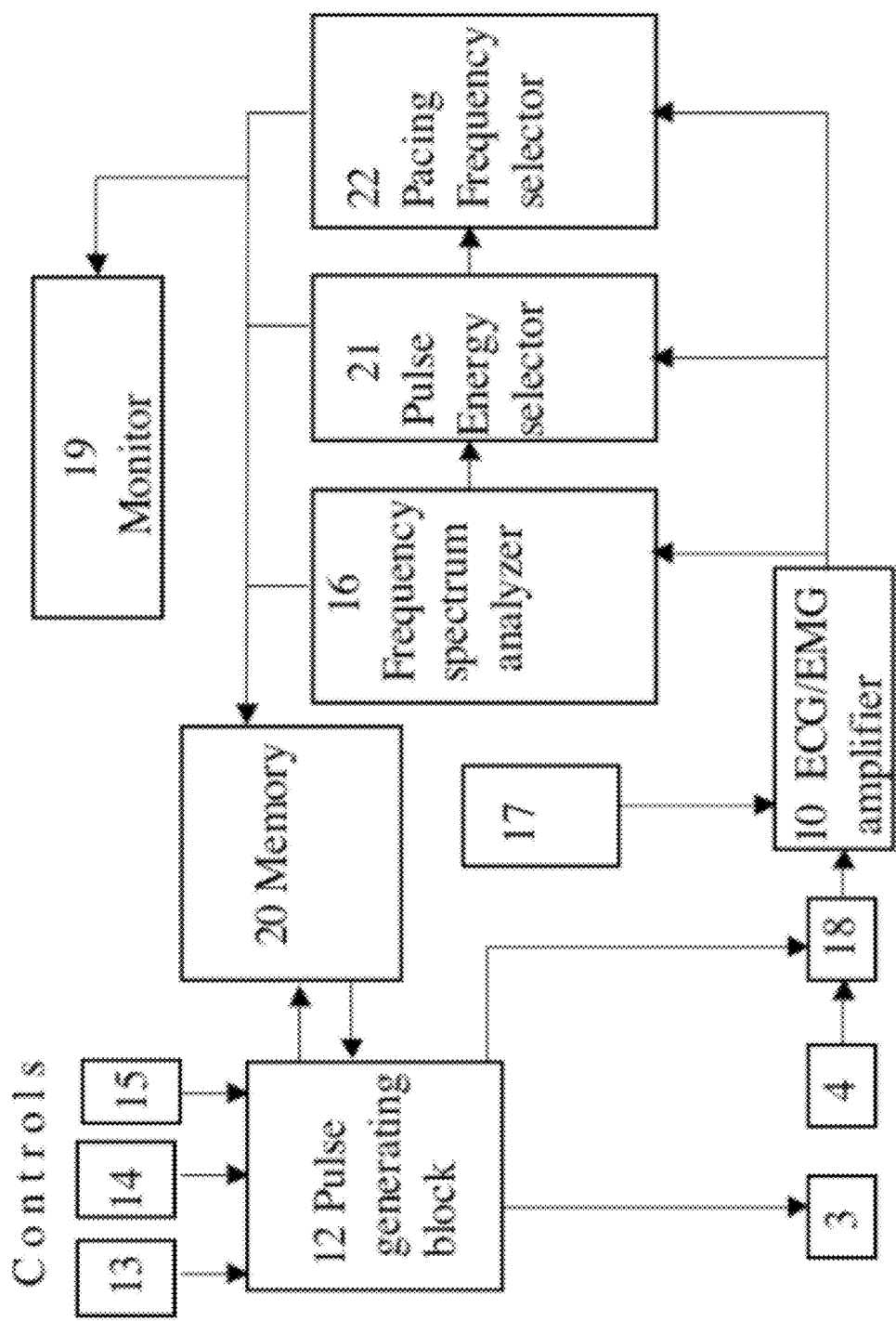

FIG. 6 is a flow chart illustrating the AFP external device of FIG. 5 in more detail. A frequency spectrum analyzer 16 transfers data to a pulse energy selector 21 and to a pacing frequency selector 22. The items schematically depicted in FIG. 6 for their first time are controls 13, 14 and 15 to manually set the period of the stimulating pulses, the number of pulses and the energy of each pulse, and a further switch 18.

Figure 7:
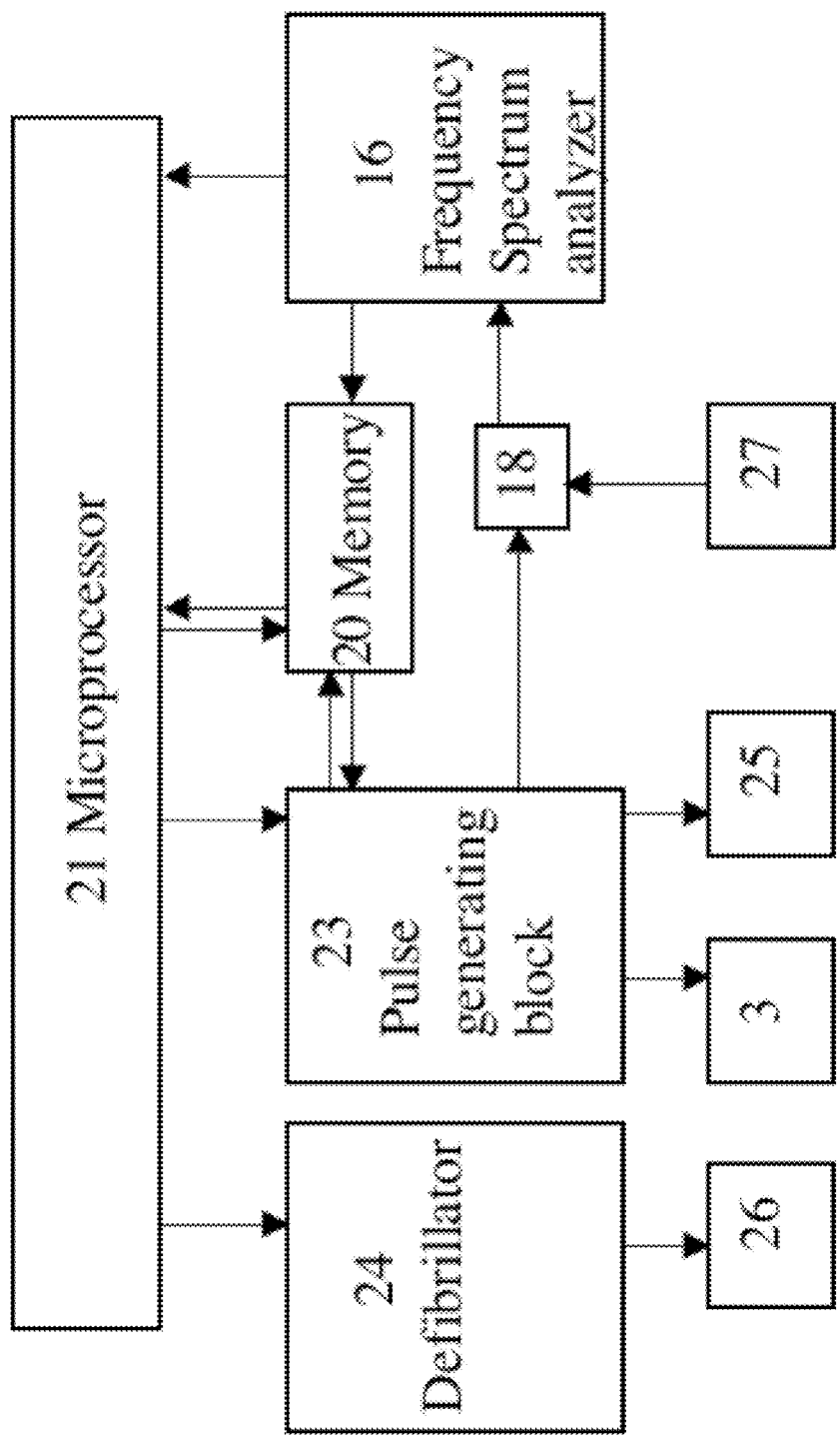

FIG. 7 is a flow chart illustrating an AFP implanted device. The frequency spectrum analyzer 16 transfers data to a microprocessor 21, and after processing in the microprocessor the data are forwarded to a pulse generating block 23. The items schematically depicted in FIG. 7 for their first time are stimulating electrode 25, defibrillating electrode 26, and sensing electrode 27.

Figure 8:
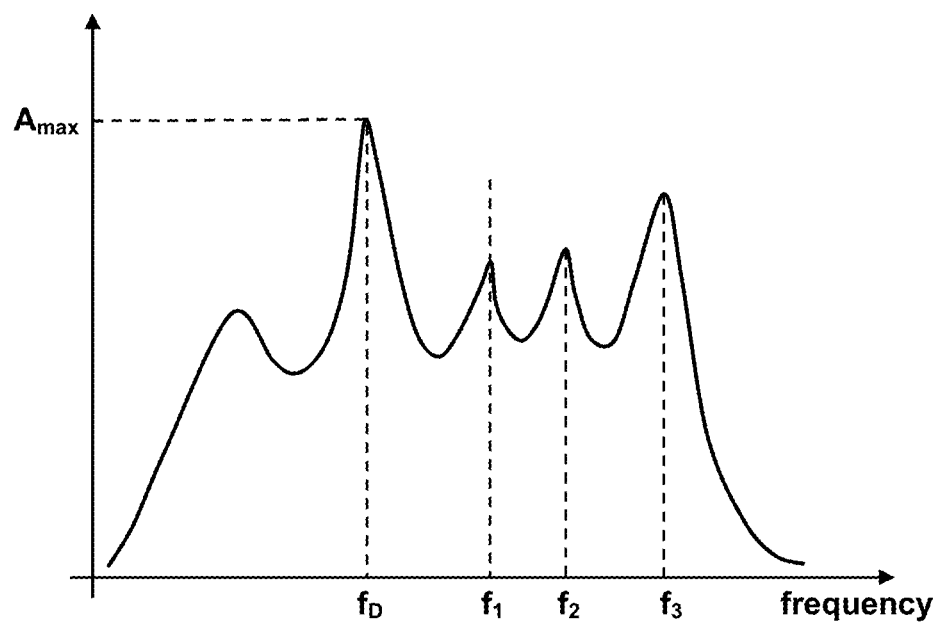

FIG. 8 is a frequency spectrum of a high frequency cardiac arrhythmia or fibrillation of a heart displaying three highest frequencies f_1, f_2, f_3 and a dominant frequency f_d.

Figure 9:
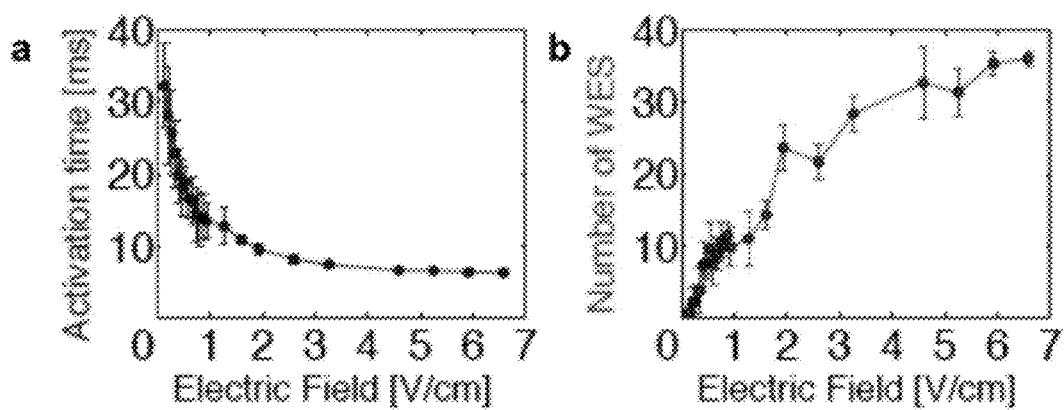

FIG. 9 illustrates the dependence of the number of effective pacing sites or wave sources (WES) as a function of electric field strength E (panel b). The increase of WES with E corresponds to a decrease in activation time, i.e. the time it takes to activate the entire heart tissue (see panel a).

DETAILED DESCRIPTION

The present invention enables pacing by electric field pulses to terminate high frequency arrhythmias. AFP permits to terminate AF and VF with a pulse energy which is one to two orders of magnitude smaller than that of cardioversion or defibrillation. In AFP, numerous heterogeneities naturally existing in the heart are used as effective pacing sites or virtual electrodes. The size distribution of natural heterogeneities in the heart is wide: it extends from microns to millimeters. This permits to control the number of effective pacing sites from 1 or 2 to dozens.

The basic physical mechanism exploited in AFP is well known in cardiology: it is a change of membrane potential by an electric field near to defects or heterogeneities. This phenomenon has been designated as "virtual electrodes" (Sepulveda, N G, Roth, B J, Wikswo, J P. Current injection into a two-dimensional anisotropic bidomain. Biophys J, 55(5), 987-99, 1989). Virtual electrodes are believed to play an important role in defibrillation, exist in all tissues and thus terminate all propagating waves. Creating a large size virtual electrode by cutting the cardiac tissue with a blade in order to decrease the pacing threshold almost to a half when pacing from a small fixed wire electrode has been proposed in U.S. Pat. No. 7,142,928.

An electric field, applied to the heart creates depolarized and hyperpolarized regions near every heterogeneity in the heart, corresponding to redistributions of the intracellular and extracellular currents. If the induced depolarization is above a threshold, it can induce a propagating excitation wave. This mechanism has been used in cardiology to explain how defibrillation works. The invention proposes to use this effect for creating as many effective pacing sites as needed, from 1 or 2 to dozens, and to use them to terminate fibrillation. In experiments using cardiac muscle preparations, the inventors verified that 1 or 2 effective pacing sites were induced by one pulse having an electric field amplitude of as low as 0.15 to 0.25 V/cm, 3 to 5 effective pacing sites were induced with 0.25 to 0.35 V/cm, and dozens of effective pacing sites were induced with 0.35 to 0.5 V/cm. For comparison: the electric field needed for conventional defibrillation is about 6 V/cm. Thus, the electric field needed to induce dozens of effective pacing sites is more than 10 fold smaller than the electric field needed for conventional defibrillation. Since the electric energy W is proportional to the square of the electric field E ($W \sim E^2$), the electric energy per pulse is even 100 fold smaller than the energy of a conventional defibrillation shock.

Figure 1:
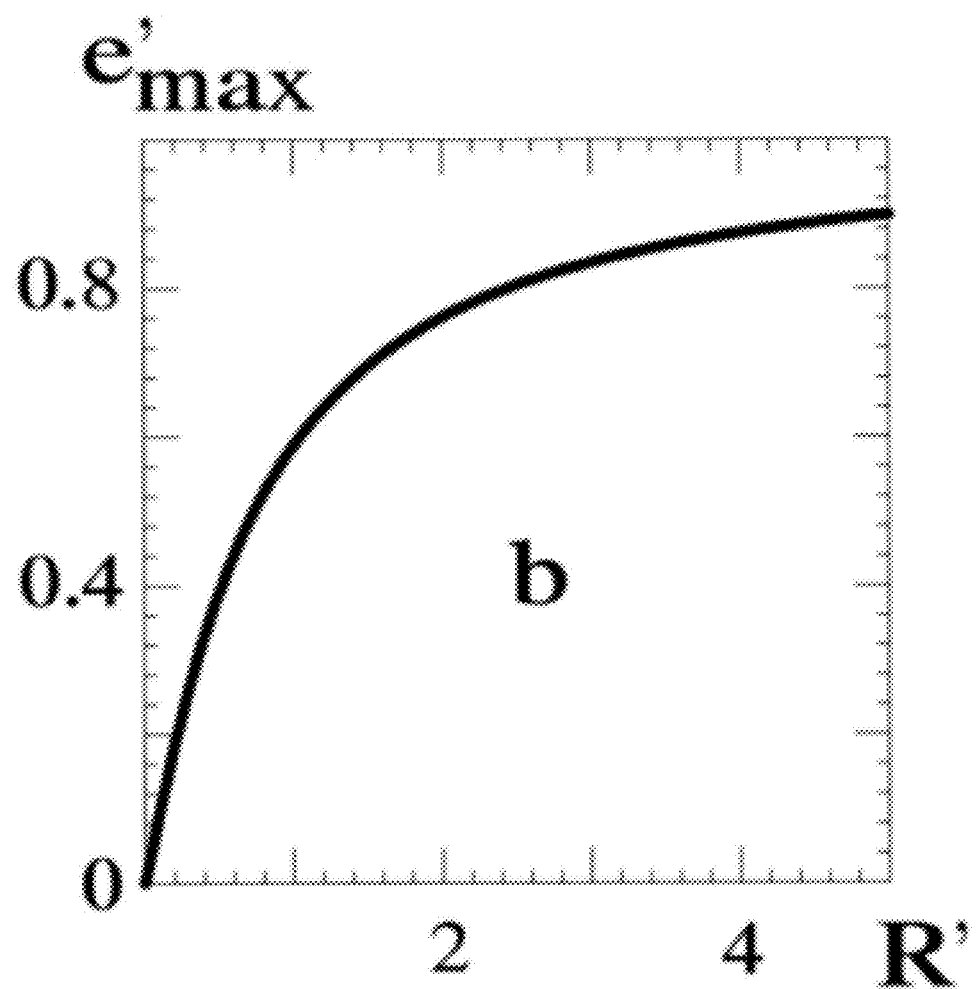
FIG. 1 illustrates that the larger a size R' of an obstacle, the larger is a depolarization $e'_{max}$ induced near to it by an electric field. Dimensionless coordinates: Obstacle size $R'=R/\lambda$, wherein R is the obstacle size in mm, $\lambda \sim 0.5$ mm is the electronic constant of the tissue. Depolarization $e'_{max}=e/e_{max}$, wherein e is the depolarization in mV, $e_{max}$ is the depolarization near to a very large obstacle. The depicted data result from an analytical solution of a linearized (LR) model according to A. Pumir, V. Krinsky, Unpinning of a rotating wave in cardiac muscle by an electric field. J. Theor. Biol, 199, 311-319, 1999.

Now referring in greater detail to the drawings, FIG. 1 illustrates that the larger the size R' of the obstacle the larger is the depolarization induced by an electric field near to it. Pulses of electric field of small amplitude induce pacing only from large size heterogeneities (see FIG. 2a). Increasing the amplitude of the electric field results in pacing also being induced from smaller, i.e. less intense, heterogeneities and from heterogeneities of a smaller size (see FIG. 2b, c). For obstacles of generic shape (not circular), the orientation of the electric field affects the position and the number of the effective pacing sites (see FIG. 2d, e).

Figure 2:
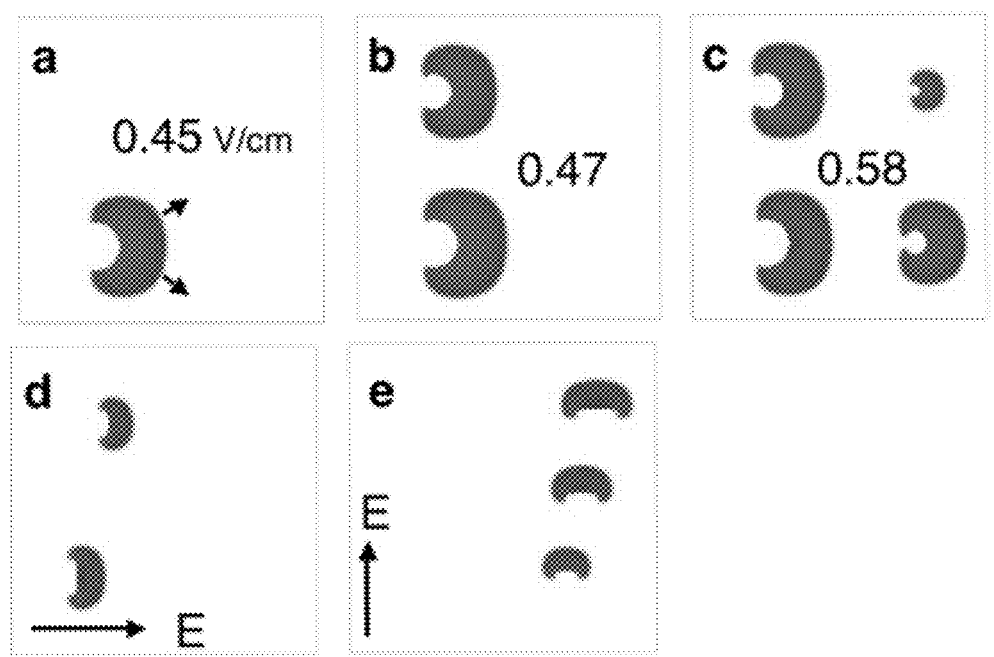
FIG. 2 illustrates how to increase a number of pacing sites by increasing an electric field (a-c), and to modify positions of pacing sites by changing a direction of the electric field (d, e). From a) to c) the electric field is increased. a) E=0.45 V/cm—pacing from 1 virtual electrode or pacing site. Short arrows indicate a direction of a propagation of a pacing wave. The pacing wave looks like a moon since it is initiated near to a circular obstacle. Further away from the obstacle, the pacing wave has a circular shape, as usual. b) E=0.47 V/cm—pacing from 2 virtual electrodes or pacing sites. c) E=0.58 V/cm—pacing from 4 virtual electrodes or pacing sites.

FIGS. 1 and 2 both demonstrate that (i) increasing the intensity of the electric field applied in a fixed direction leads to wave emission from an increasingly large set of heterogeneities in the tissue, and that (ii) changing the direction of the applied electric field leads to wave emission from different sets of heterogeneities in the tissue. These aspects of the present invention permit to realize multisite heart pacing with adjustable number of effective pacing sites.

From a conventional point of view, the method of the present invention should not be able to terminate AF or VF due to the very low energy of the electric field pulses used. However, the method of the present invention does terminate AF and VF activating a multitude of effective pacing sites in the heart.

In majority of biological applications of a multisite pacing, important is to reach a desired effect, say, increase the contraction force of a damaged heart to the needed level. Then, the contraction force is measured. Adjusting the number of pacing sites can be achieved in several successive steps. If the contraction force is below the needed level, the electric field amplitude will be increased, and the contraction force measured again. If the force is not enough, the electric field amplitude will be increased again. If the force is more than needed, the electric field amplitude will be decreased. If the measured contraction force is enough, this electric field amplitude will be kept. In such cases, adjusting the number of pacing sites is achieved without measurement the actual number of pacing sites, my measuring the biological effect.

The actual number of activated pacing sites in the heart, may be estimated based on measuring the propagation time of a single pacing pulse to reach a detection electrode. For a fiber, wherein a pacing and detecting electrodes are connected to the ends of the fiber, the propagation time t_1 at which a pulse delivered by the pacing electrode reaches the detecting electrode is t_1=L/C, wherein L is the fiber length and C is the pulse propagation velocity.

If N pacing sites are homogeneously distributed over the fiber, the distance between the detecting electrode and the nearest pacing site is L_N=L/N. If an electric field pulse applied by the pacing electrode activates all pacing sites in the fiber, the propagation time t_p of a pulse to reach the detecting electrode will be the propagation time from this nearest pacing site, i.e. t_p=L/CN (compare FIG. 9 panel a). From this equitation, the number N of pacing sites can be derived as N=L/(C t_p). For two-dimensional and three-dimensional propagation, similar formulas are easily obtained. The relation between the propagation time from the nearest pacing site, i.e. the activation time of the entire tissue and the number of pacing sites is a key to closed loop control of the number of pacing sites.

The electric field in the electric field pulses should not exceed 6 V/cm. With an electric field higher than 6 V/cm, the whole heart, i.e. all of the heart tissue is excited simultaneously (6 V/cm is the electric field value of common defibrillating), and any further increase in electric field will not increase the number of effective pacing sites.

Changing location of the pacing sites can be achieved by changing orientation of the electric field. A change of orientation of the electric field may both be achieved by switching between a plurality of pacing electrodes connected to the heart at different locations and by switching between a plurality of ground electrodes which may be provided extrathoracally or even extracorporally. These ground electrodes serve as counter electrodes to the at least one pacing electrode. They may be paddle or other large surface electrodes to keep low the current density at the electrode surface.

In the following, the AFP method according to the present invention will be compared to ATP.

Conventional ATP is only successful against low frequency arrhythmias, and its success rate fast decreases with increasing frequency of the arrhythmia. The physical reason for the inability of ATP to terminate high frequency arrhythmias is that with low frequency pacing, all pacing waves propagate over the whole heart, but that with high frequency pacing, the propagation of the high frequency waves over the whole heart cannot be sustained.

The high frequency waves decay with increasing distance from the pacing electrode by which they are applied to the heart. Due to the Wenckebach rhythm transformation, every second wave (more rarely, every third wave) decays generically. Thus, only near to the pacing electrode, the frequency of the propagating waves is the frequency of the pacing pulses; at a distance to the pacing electrode, the frequency of propagating waves becomes lower. These low frequency waves are only able to capture low frequency arrhythmias, but no high frequency arrhythmias.

To terminate a high frequency pathological source of waves, the pacing electrode should be situated close to it. With conventional fixed pacing leads, this will be achieved by chance only. Pacing from cardiac heterogeneities, however, permits to regulate the number and the position of pacing sites, and thus to avoid this problem.

FIGS. 3 and 4 numerically illustrate how, for geometrical reasons, a conventional fixed pacing lead may fail to pace away a set of rotating waves, whereas virtual electrodes in the tissue permits to pace away a set of rotating waves. In FIG. 3, only one heterogeneity is used for pacing is shown.

An embodiment of an AFP external device 1 according to the present invention is schematically shown in FIG. 5 together with a defibrillator 7 and an ATP external device 5. More details of the AFP external device 1 according to the present invention are shown in FIG. 6. The device 1 for controlling high frequency cardiac arrhythmias consists of the following main parts: a pulse generating block 12, an arrhythmia frequency spectrum analyzer 16, a pulse energy selector 21, and a pacing frequency selector 22. Pulse generating block 12 is tuned by control devices 13, 14, 15 to manually set the period of the pulses, the number of pulses and the energy of a pulse. The pulse generating block 12 is connected to a defibrillating or pacing electrode 3, to a switch 18 and to a memory 20. The Pulse generating block 12 of the AFP external device 1 according to the present invention is different to that one of the cardioverter/defibrillator 7 and that one of the ATP pacemaker 5 in that it is able to deliver pulses at time interval much shorter than usually needed to charge a capacitor of the defibrillator and to pace from defibrillating electrodes, and in that it supplies 1 to 2 orders of magnitude less pulse energy than a defibrillator.

In an embodiment of the invention, the defibrillating or pacing electrode 3 is an intracardiac catheter defibrillating electrode. In another embodiment of the invention, it may be an implanted intracardiac electrode. External defibrillating patches may also be used as pacing electrodes, but not in cases in which pacing pulses below the pain threshold are to be applied.

Pulse Energy selector 21 obtains data from an ECG/EMG amplifier 10 and is connected to the memory 20. Pacing Frequency selector 22 obtains data from ECG/EMG amplifier 10 and is connected to the memory 20. Pacing Frequency selector 22 sends data to a monitor 19 including recommendations to a clinician with regard to the values to be set for the period of the pulses, the number of pulses and the energy of a pulse.

Arrhythmia frequency spectrum analyzer 16 obtains data from ECG/EMG amplifier 10 and is connected to the memory 20. Frequency spectrum analyzer 16 is intended to (i) help to choose the pacing frequency for pacing from virtual electrodes, and (ii) protect against delivering an electric field pulse near the T wave on the ECG.

Function (i) is needed since during AF the EMG/ECG records are not periodic, and the choice of the pacing interval even by a well trained medical personnel may be erroneous. In a stationary device, the analyzer on line supplies frequencies and amplitudes of 3 largest peaks in the Fourier spectrum of the arrhythmia, and the whole Fourier spectrum.

Function (ii) provides for an additional protection against induction of VF when AFP is applied in atria. Usually, synchronization of the cardioverter/defibrillator with the R wave is used. But since AFP delivers several electric field pulses, all of them cannot be synchronized with the R wave. Instead, the EMG/ECG automatic analyzer for AFP protects against delivering an electric field pulse near the T wave in the ECG.

The frequency of the electric field pulses may be selected from about 0.9 to about 1.1 times an arrhythmia characteristic frequency. This characteristic frequency may be selected from the three largest or highest peaks in the Fourier spectrum of the arrhythmia. Preferably, it is selected from the three peaks in the Fourier spectrum which display the highest frequency. These three peaks may or may not (see FIG. 8) include a dominant frequency that displays the highest amplitude in the Fourier spectrum.

FIG. 7 is a block diagram of an implanted device according to the present invention. Pulse generating block 23 delivers pulses either via an implanted ATP electrode 25 or from defibrillation electrodes 3. For pacing from an implanted electrode, it chooses standard pacing amplitudes commonly applied for ATP.

For pacing from defibrillation electrodes, the pulse generating block 23 allows for choosing the energy of the pulses from 0.01 J to 1 J for intracardiac defibrillating electrodes, the time interval between the pulses from 100 ms to 250 ms, and the number of pulses from 4 to 8 pulses.

Pulse generating block 23 receives data from microprocessor 21 and operates a switch 18. In an implanted device, Frequency spectrum analyzer 16 contains several band pass filters to avoid overloading of a microprocessor with calculations of Fourrier spectra. Frequency spectrum analyzer 16 obtains data from sensing electrode 27 and sends data to memory 20 and to microprocessor 21. Microprocessor 21 selects the pulse energy and the pacing frequency and sends these data to the pulse generating block 23. Microprocessor 21 also operates a defibrillator 24.

An advantageous embodiment of the invention comprises an external AFP device which is usable for clinical investigations. AFP is applied if an arrhythmia with frequency higher than that permitting to use ATP is detected. In cases suitable for the application of AFP, the frequency of the arrhythmia is above the threshold for ATP but not by more than 50%.

FIG. 5 is a block diagram illustrating an embodiment of controlling high frequency cardiac arrhythmias by anti-fibrillation pacing (AFP) external device 1. AFP External Device 1 is coupled to a patient's heart 2 via a diagnostic catheter 4 and defibrillating electrode 3, that may either be an implanted defibrillating electrode or a catheter. ATP external device 5 is connected to the patient's heart 2 via a catheter 6 comprising monopolar or bipolar stimulating electrodes. Defibrillator 7 is connected to the patient's chest 9 via paddle electrodes 8. ECG amplifier 10 is connected to ECG electrodes 11 via switch 17. Switch 17 disconnects ECG amplifier 10 from ECG electrodes 11 when AFP external device 1 delivers AFP pulses to the heart.

FIG. 6 is a block diagram illustrating AFP external device. Pulse generating block 12 is connected to defibrillating electrode 3. Controls 13, 14, 15 are connected to pulse generating block 12. The controls 13, 14, 15 permit to manually set the period or frequency of the stimulating pulses (control 13), the number of pulses (control 14) and the electric energy of each pulse (control 15). Frequency spectrum analyzer 16 is connected to ECG amplifier 10 and diagnostic catheter via switch 18. Switch 18 disconnects ECG/EMG amplifier 10 from diagnostic catheter 4 when Pulse generating block 12 delivers AFP pulses to the heart.

Frequency spectrum analyzer 16 selects several (e.g., 3) highest frequencies $f\_i$, $i=1, 2, 3$ from the real time arrhythmia frequency spectrum, an exemplary example of which is depicted in FIG. 8. Pacing Frequency selector 22 determines the number of pulses N and the pacing frequency F to complete scanning of the phase spaces of 3 wave sources (rotating waves) emitting waves with frequencies $f\_i$, to hit their Vulnerable Windows (VW) and terminate them. A skilled person can propose different algorithms to achieve this. Below is an illustrative example.

Example: Calculate $dT\_2-1=T\_2-T\_1$, $dT\_3-2=T\_3-T\_2$, $dT\_3-1=T\_3-T\_1$, wherein $T\_i=1/f\_i$, $i=1, 2, 3$. Calculate the minimal number of pulses N needed to scan the entire phase space $N\_1=2T\_1/dT\_1-2$, $N\_2=2T\_2/dT\_1-2$.

If $4<N\_1$, $N\_2<10$, set $F=2/(T\_1+T\_2)$, $N=N\_2$.

If $4≥N\_1$, $N\_2$, set $F=0.8/T\_1$, $N=5$.

If $N\_1$, $N\_2>10$, calculate $N\_3=2T\_3/dT\_3-2$.

If $4<N\_3<10$, set $F=2/(T\_2+T\_3)$, $N=N3$.

If $N\_3>10$ set $F=2.4/(T\_1+T\_2+T\_3)$, $N=1+T3/[0.42(T\_2+T\_3)-0.58\ T\_1)]$.

If $4≥N\_3$, set $F=1.6/(T\_1+T\_2)$, $N=1+T\_2/(0.625\ T\_2-0.375\ T\_1)$.

The same approach can be used for a number of highest frequency peaks higher than 3.

In an AFP implanted device, FIG. 7, frequency spectrum analyzer 16 transfers data to memory 20 and microprocessor 21. Microprocessor 21 selects pulse energy, pacing frequency and the number of pulses, and transfers them to the Pulse generating block 23.

Microprocessor 21 in FIG. 7 determines several highest frequencies ($f\_i$) from the real time frequency spectrum. Microprocessor 21 in FIG. 7 selects the pacing pulse energy in the range 1/400-1/2 of the state of art defibrillation energy.

Frequency spectrum analyzer 16 is connected to monitor 19 where it displays the Fourier spectrum of AF or other high frequency arrhythmia to help medical personnel to chose pacing frequency for ATP or AFP. Pulse generating block 12 and Frequency spectrum analyzer 16 are connected to memory 20.

AFP External Device 1 may be realized as a box, i.e. as a single unit containing all these elements, or it can use an external PC as ECG/EMG analyzer 16, memory 20 and monitor 19.

FIG. 7 is a flow chart illustrating AFP implanted device. Pulse generating block 23 is connected to the heart via defibrillating electrode 3 when it delivers AFP pacing and via stimulating electrode 25 when it delivers ATP pacing. Defibrillator 24 is connected to the heart via defibrillating electrode 26 which may be the same as the defibrillating electrode 3. Frequency spectrum analyzer 16 is connected to the heart via sensing electrode 27. All is controlled by Microprocessor 21.

The AFP method of the present invention has been successfully tested against fibrillations both in vivo and in vitro experiments. The required pulse energies for terminating AF were 0.15 J in vivo and 0.08 J in vitro; and the required pulse energy for terminating for VF was 0.14 J in vitro. These energies are actually measured data.

Comparison of the Method of the Present Invention with Other Patents:

Kroll U.S. Pat. No. 7,809,439 B2 describes a conventional multisite pacing, i.e., for pacing from, say, 5 sites he needs 5 leads. Kroll describes also one lead, but he uses it to pace from one site only. He does not use or anticipate creation and control of several pacing sites with one lead only.

Kroll describes fibrillation termination. Kroll presents no experimental tests of his approach to arrhythmias termination, thus it is not possible to compare effectiveness of his method with the method of the present invention.

Sweeney U.S. Pat. No. 4,996,984, U.S. Pat. No. 8,000,786 B2 describes an approach to terminate fibrillation based on time intervals associated with the fibrillation cycle length. He describes also experimental tests of his approach on $n=2$ animals. Sweeney's minimal defibrillation energy is 2.7-3 J. The average fibrillation termination energy in the method of the present invention is 0.14 J, i.e. ~20 times less (obtained on $n=8$ animals).

Mechanism Underlying and Advantages of the Method of the Present Invention:

The Fourier spectrum contains information about frequencies of several fastest rotating waves. This information is needed to complete scanning of their phase spaces. Thus, the vulnerable window (VW) of every one of them is hit by a scanning pulse, terminating every of one them. No prior art method known to the inventors uses Fourier spectrum to select parameters of pacing to terminate fibrillation.

More Detailed Explanation of the Mechanism:

A necessary condition to terminate a rotating wave "i" by scanning its phase space and hitting its VW is: the pacing period T should be not close to its rotation period $T\_i$. The information needed for this is contained in the Fourier spectrum.

Examples a) and b) below illustrate it:

a) For 3 selected fastest rotating waves with periods T1=90 ms, T2=100 ms, T3=110 ms, if the chosen pacing period is 101 ms, then the phase space of the wave 2 will be scanned with the scanning step $t\_1$=101 ms-100 ms=1 ms. Then, to scan the entire phase space of the wave 2, the number of pulses needed $N\_2$=100 ms: 1 ms=100 pulses. Such a big number of pulses cannot be used. But with any number of pulses $N<100$, the scanning of the phase space of wave 2 will not be completed. Hitting its VW with a pacing pulse and thus termination of the rotating wave cannot be guaranteed.

b) If the chosen pacing period is close to 90 ms, or to 110 ms, then required number of pulses N_1 or N_3 will be unrealistically large. Many variations and modifications may be made to the preferred embodiments of the invention without departing substantially from the spirit and principles of the invention. All such modifications and variations are intended to be included herein within the scope of the present invention, as defined by the following claims.

We claim:

1. A method of terminating high frequency cardiac arrhythmias and fibrillations by multisite electric field pacing of a heart, the method comprising:
   determining whether a high frequency cardiac arrhythmia or fibrillation of the heart has a frequency higher than permitting anti tachycardia pacing (ATP) of the heart, wherein, if the high frequency cardiac arrhythmia or fibrillation of the heart has a frequency higher than permitting anti tachycardia pacing (ATP) of the heart, the method further comprises:
      determining a real time Fourier spectrum of the high frequency cardiac arrhythmia or fibrillation of the heart;
      selecting several highest frequencies f_i in the Fourier spectrum;
      selecting a pacing pulse energy from about 0.01 to about 1 Joules;
      selecting pacing parameters, including a number of pulses N and a pacing frequency F, based on the several determined highest frequencies f_i in the Fourier spectrum; and
      delivering the pulses to the heart to terminate the high frequency cardiac arrhythmia or fibrillation.

2. The method of claim 1, wherein the pacing frequency F differs by at least about 5% from any of the determined highest frequencies.

3. The method of claim 1, wherein the number N of pacing pulses is selected as N=max(N_i, i=1,2, . . ., n), where N is the number of pulses needed to complete scanning of the phase space of the rotating wave with frequency f_i, and to hits its vulnerable window with at least one pulse.

4. The method of claim 3, wherein n =3.

5. The method of claim 1, wherein the pacing frequency F is chosen to minimize number N of pacing pulses, or to keep them within $2 \leq N \leq 10$.

6. An anti fibrillation pacing (AFP) method of terminating high frequency cardiac arrhythmias and fibrillations, the method comprising:
   determining whether a high frequency cardiac arrhythmia or fibrillation of a heart has a frequency higher than permitting anti tachycardia pacing (ATP) of the heart, where, if the high frequency cardiac arrhythmia or fibrillation of the heart has a frequency higher than permitting anti tachycardia pacing (ATP) of the heart, the method further comprises:
      determining a real time Fourier spectrum of the high frequency cardiac arrhythmia or fibrillation of the heart;
      selecting several highest frequencies f_in the Fourier spectrum;
      selecting a frequency of electric field pacing pulses based on the several determined highest frequencies f_i in the Fourier spectrum;
      selecting an energy of the electric field pacing pulses from about 0.01 to about 1 Joules;
      selecting an amplitude of the electric field pacing pulses from about 0.15 to about 0.5 V/cm to activate a multitude of heterogeneities naturally existing in the heart as effective pacing sites in the heart tissue by each of the electric field pacing pulses; and
      delivering 4 to 8 of the electric field pacing pulses having the selected frequency, energy and amplitude to the heart.

* * * * *